United States Patent [19]

Krause et al.

[11] Patent Number: 4,945,177
[45] Date of Patent: Jul. 31, 1990

[54] ANTIMICROBIALLY ACTIVE NITRILES AND THE PRODUCTION THEREOF

[75] Inventors: Horst-Juergen Krause; Hans-Theo Leinen, both of Duesseldorf; Rudolf Lehmann, Leichlingen, all of Fed. Rep. of Germany

[73] Assignee: Henkel Kommanditgesellschaft auf Aktien, Duesseldorf-Holthausen, Fed. Rep. of Germany

[21] Appl. No.: 3,425

[22] PCT Filed: Apr. 16, 1986

[86] PCT No.: PCT/EP86/00220
§ 371 Date: Feb. 11, 1987
§ 102(e) Date: Feb. 11, 1987

[87] PCT Pub. No.: WO86/06369
PCT Pub. Date: Nov. 6, 1986

[30] Foreign Application Priority Data

Apr. 24, 1985 [DE] Fed. Rep. of Germany ....... 3514688

[51] Int. Cl.$^5$ ................ C07C 119/00; C07D 279/12; C07D 265/30
[52] U.S. Cl. .................................. 558/405; 558/432; 558/433; 558/434; 558/440; 544/58.4; 544/163; 544/334; 544/335; 544/402; 540/607; 540/610; 546/315; 546/328; 548/540
[58] Field of Search ............... 558/405, 432, 433, 434, 558/440

[56] References Cited

FOREIGN PATENT DOCUMENTS

| | | |
|---|---|---|
| 0089011 | 9/1983 | European Pat. Off. ............ 558/405 |
| 0213841 | 3/1987 | European Pat. Off. ............ 558/271 |
| 0224725 | 6/1987 | European Pat. Off. ............ 558/271 |
| 3525015 | 1/1986 | Fed. Rep. of Germany ...... 558/271 |
| 2239456 | 2/1975 | France ................. 558/405 |
| 1603076 | 11/1981 | United Kingdom ............... 558/271 |

OTHER PUBLICATIONS

Chem. Abstracts, Gault et al., vol. 61; 14523d, No. 12, (1964).
Mikolajczyk et al., Chem. Abstracts, vol. 83, No. 13; 113818e, (1975).
Methoden der Organischen Chemie, pp. 573–574 (1972).
Chem. Abstracts, Bodalski et al., vol. 84, No. 23, 164406x (1976).
Block, R., Chem. Abstracts, vol. 65; 18493g (1966).
Patents Abstracts of Japan, vol. 10, No. 172 (1986) 85 C 354.

Primary Examiner—Richard A. Schwartz
Assistant Examiner—J. Richter
Attorney, Agent, or Firm—Ernest G. Szoke; Wayne C. Jaeschke; Henry E. Millson, Jr.

[57] ABSTRACT

Novel 2,2-dibromo-3-oxonitriles of Formula I,

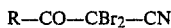

R—CO—CBr$_2$—CN    (I)

in which R represents in each case a possibly substituted or unsubstituted aliphatic, cycloaliphatic, aromatic or heterocyclic group, with the exception of a phenyl group substituted with 1 to 3 chlorine atoms, can be obtained in that a carboxylic acid ester of Formula II

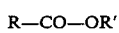

R—CO—OR′    (II)

in which R has the significance indicated for Formula I, and in which R′ represents a straight chain or branched alkyl group with 1 to 4 carbon atoms, is reacted with acetonitrile in the presence of a strong base, the 3-oxonitrile produced is isolated from the reaction mixture and reacted in a solvent inert with respect to bromine and in the presence of a hydrogen bromide acceptor, possibly under cooling, and the 2,2-dibromo-3-oxonitrile of Formula I obtained is isolated from the reaction mixture.

3 Claims, No Drawings

ANTIMICROBIALLY ACTIVE NITRILES AND THE PRODUCTION THEREOF

The invention pertains to antimicrobially active 2,2-dibromo-3-oxonitriles of Formula I, $$R—CO—CBr_2—CN \qquad (I)$$

in which R represents in each case a possibly substituted or unsubstituted aliphatic, cycloaliphatic, aromatic or heterocyclic group, with the exception of a phenyl group substituted with 1 to 3 chlorine atoms.

The invention also pertains to a process for producing 2,2-dibromo-3-oxonitriles of Formula I, in which a carboxylic acid ester of Formula II, $$R—CO—OR' \qquad (II)$$

in which R has the significance indicated for Formula I, and in which R' represents a straight chain or branched alkyl group with 1 to 4 carbon atoms, is reacted with acetonitrile in the presence of a strong base, the 3-oxonitrile produced is isolated from the reaction mixture and reacted with bromine in a solvent inert to bromine and in the presence of a hydrogen bromide acceptor, possibly under cooling, and the 2,2-dibromo-3-oxonitrile of Formula I produced is isolated from the reaction mixture.

From *Chemical Abstracts*, Abstract No. 84:164406x (1976), compounds of Formula I are known, in which R represents a phenyl group substituted with 1 to 3 chlorine atoms; this literature reference contains no mention of the antimicrobial activity of this class of substances.

The use of the 2,2-dibromo-3-oxonitriles of Formula I as antimicrobial active ingredients is not claimed here; instead, this forms the subject matter of the applicant's German Patent Application P35 14688.5 (D7237), submitted simultaneously [with this].

In particular, in the above mentioned Formula I, R can represent a straight chain or branched alkyl group with 3 to 19 carbon atoms, a cycloaliphatic residue with 3 to 6 ring hydrocarbon [sic] atoms, possibly substituted with alkyl groups and/or halogen atoms, a phenyl or naphthyl group possibly substituted with alkyl groups, alkoxy groups, fluorine or bromine atoms, and/or nitro groups, or a 5-or 6-membered heterocyclic group containing oxygen, sulfur or nitrogen atoms.

Suitable starting materials for the production of the 2,2-dibromo-3-oxonitriles of Formula I in accordance with the process stated in the preceding include, for example, esters of the following carboxylic acids: butyric acid, valerianic acid, caproic acid, caprylic acid, capric acid, lauric acid, myristic acid, palmitic acid, stearic acid, arachidic acid, behenic acid, lignoceric acid, pivalic acid, 2,2-dimethylbutyric acid, 2,2-dimethylvalerianic acid, 2-ethylhexanecarboxylic acid, cyclopropanecarboxylic acid, 1-methylcyclopropanecarboxylic acid, 2-ethylcyclopropanecarboxylic acid, cyclobutanecarboxylic acid, 2-methylcyclopropanecarboxylic acid, 3-propylcyclobutanecarboxylic acid, cyclopentanecarboxylic acid, 1-ethylcyclopentanecarboxylic acid, 2-methylcyclopentanecarboxylic acid, 3-propylcyclopentanecarboxylic acid, cyclohexanecarboxylic acid, 1-methylcyclohexylcarboxylic acid, 2-methylcyclohexanecarboxylic acid, 3,4-dimethylcyclohexanecarboxylic acid, 2,2-dichloro-1-methylcyclopropanecarboxylic acid, benzoic acid, 2-methylbenzoic acid, 3-methylbenzoic acid, 4-methylbenzoic acid, 2,4-dimethylbenzoic acid, 2-fluorobenzoic acid, 3-fluorobenzoic acid, 4-fluorobenzoic acid, 2-bromobenzoic acid, 3-bromobenzoic acid, 4-bromobenzoic acid, 2,4-dibromobenzoic acid, 2,5-dibromobenzoic acid, 2-methoxybenzoic acid, 2-ethoxybenzoic acid, 3-methoxybenzoic acid, 4-methoxybenzoic acid, 3,4-dimethoxybenzoic acid, 2-nitrobenzoic acid, 3-nitrobenzoic acid, 4-nitrobenzoic acid, 2,4-dinitrobenzoic acid, 2,5-dinitrobenzoic acid, 3,5-dinitrobenzoic acid, 2-trifluoromethylbenzoic acid, 4-trifluoromethylbenzoic acid, 1-naphthalenecarboxylic acid, 2-naphthalenecarboxylic acid, furan-2-carboxylic acid, furan-3-carboxylic acid, 5-bromo-2-methylfuran-3-carboxylic acid, tetrahydrofuran-2-carboxylic acid, thiophene-2-carboxylic acid, thiophene-3-carboxylic acid, 5-methylthiophene-2-carboxylic acid, tetrahydrothiophene-3-carboxylic acid, picolinic acid, nicotinic acid and isonicotinic acid.

The alcohol component of the carboxylic acid ester of the Formula II can consist of methanol, ethanol, n-propanol, i-propanol, n-butanol, i-butanol, sec-butanol and tert-butanol, wherein methyl esters are particularly preferred.

The first step of the above described process involves the condensation, known from organic synthesis, of carboxylic acid esters with carboxylic acid nitriles, in which the corresponding 3-oxonitriles can be obtained in the presence of strong bases. As strong bases, in accordance with statements of the relevant literature, finely divided sodium amide and sodium hydride especially come under consideration (see Houben-Weyl: *Methods of Organic Chemistry (Methoden der organischen Chemie)*, Vol. 8, pp. 574–575; German Preliminary Published Application No. 2,309,472). In contrast to the statements in Houben-Weyl it was possible to show in connection with this invention that the condensation of fatty acid esters with acetonitriles can also be carried out with sodium methylate as the base if a larger excess of acetonitrile is used and the alcohol forming during the condensation reaction is continuously distilled off from the reaction mixture together with acetonitrile.

If sodium amide or sodium hydride is used as the condensation agent, the quantity of acetonitrile used in the reaction is generally between 1.0 and 2.0 mol per mol of the carboxylic acid ester used. If sodium methylate is used as the condensation agent, 10 to 20 mol acetonitrile per mol carboxylic acid ester are advantageously used.

The base intended for use as the condensation agent is advantageously used in quantities of 1 to 2 mol per mol of the carboxylic acid ester present.

When sodium amide or sodium hydride is used as the condensation agent, the reaction is advantageously carried out in an inert solvent, wherein ethers and aliphatic or aromatic hydrocarbons such as cyclohexane, benzene, toluene or xylene come under consideration. When sodium methylate is used, in general no solvent is added aside from the methanol normally introduced with the sodium methylate.

It has proven advantageous to perform the condensation reaction in an inert gas atmosphere, for example in a nitrogen or argon atmosphere. The reaction temperature can lie in the range between 50°, preferably 60° C., and the reflux temperature of the respective reaction mixture.

In performing the condensation reaction, the mixture of carboxylic acid ester, condensation agent and, if desired, solvent is taken and heated to the intended reaction temperature. Then the acetonitrile is slowly introduced into the heated mixture, agitating vigorously. If sodium methylate is used as the strong base, a mixture of carboxylic acid esters and acetonitrile is taken, heated to the boiling point, then the sodium methylate solution slowly added. In this process the alcohol forming during the reaction and the methanol introduced with the sodium methylate are continuously withdrawn from the reaction mixture together with the acetonitrile via an appropriate distillation device.

The workup of the reaction mixture is normally accomplished by adding a sufficient quantity of water so that the solids present in the reaction mixture dissolve completely, forming a two-phase system. The aqueous phase is removed, and the organic phase is washed with additional water if desired; the separated aqueous phases are combined, cooled, and adjusted under cooling with aqueous mineral acid to a pH value between 1 and 5. In this process the 3-oxonitrile separates out as a solid or oil and can be isolated in a known manner. However, during the workup of the reaction mixture it is possible to proceed by separating the precipitate present by suction filtration, washing with a suitable solvent, and then introducing it into an aqueous mineral acid solution under vigorous agitation for neutralization. The quantity of acid is selected in this process such that at the end of the reaction the aqueous solution has a pH value between 1 and 5. Hydrochloric acid is preferred as the mineral acid.

Advantageously, during workup of the reaction mixture, the treatment with the aqueous mineral acid should be carried out at a temperature that does not exceed 10° C., preferably 0° C.

The bromination of the 3-oxonitriles obtained, carried out in the second step of the above described process for producing the compounds of Formula I, is performed with elemental bromine in a solvent inert with respect to bromine [and] in the presence of a hydrogen bromide acceptor.

Suitable solvents include chlorinated hydrocarbons, especially methylene chloride, or glacial acetic acid. The procedure using methylene chloride has proven particularly valuable, since in this case it is possible to work in a two-phase, solvent-water mixture, and the hydrogen bromide acceptor exists in dissolved form in the aqueous phase.

Bromine is preferably used in equimolar quantities, but at most in an excess of 5 to 10 mol-%. Suitable hydrogen bromide acceptors especially include weak bases, such as sodium hydrogen carbonate, potassium hydrogen carbonate, calcium carbonate or sodium acetate.

The bromination of the 3-oxonitriles is advantageously performed under cooling, wherein temperatures between −10° and +25° C. are preferred.

In performing the bromination, the 3-oxonitrile to be reacted, dissolved in the respective solvent, and the hydrogen bromide acceptor, if desired dissolved in water, are taken initially, and under vigorous agitation and possibly cooling the appropriate amount of bromine, advantageously likewise dissolved in the solvent selected, is slowly added. After the end of bromine addition the reaction mixture is advantageously agitated for an additional 3 to 4 hr at room temperature to bring the reaction to completion.

For workup of the reaction mixture, first the aqueous phase possibly present is removed; the organic phase is washed out with water. Small quantities of bromine remaining after this can be removed with the aid of sodium hydrogen sulfite or hydroxylamine hydrochloride. The organic solution is then dried with the aid of a suitable drying agent, for example anhydrous sodium sulfate, and freed from solvents. The 2,2-dibromo-3-oxonitriles remaining behind in most cases already have a degree of purity which makes it possible to convey the products directly to practical use. If desired, the products can be purified by recrystallizing or distilling in a thin layer evaporator.

Because of their microbistatic and microbicidal activity against bacteria and fungi, the substances in accordance with the invention are suitable for carrying out various disinfection and preservation tasks in the non-therapeutic sector. For use as active ingredients in antimicrobial agents, the substances in accordance with the invention can be incorporated into liquid, pasty or solid preparations. Agents of this type can be used in a great variety of areas, for example as cleaning agents, disinfectants and preservatives for textiles, floors, hospital apparatus, medical instruments, schools, swimming pools, public transport vehicles, and commercial operations such as dairies, breweries and laundries.

As a rule, the finished antimicrobial agents contain, in addition to the active ingredients described, further customarily utilized components, which are selected depending on the intended application form and the application purpose. Water and the usual organic solvents, especially alcohols and glycol ethers, if desired mixed with water, come under consideration as solvents for liquid preparations. If an additional cleaning action is desired in addition to the antimicrobial activity, the agents can contain nonionic surfactants or amphoteric surfactants. Possible nonionic surfactants include addition products of 4 to 40, preferably 4 to 20 mol ethylene oxide to 1 mol of fatty alcohol, alkylcyclohexanol, alkylphenol, fatty acid, fatty amine, fatty acid amide, or alkanesulfonamide. Particular interest lies in addition products of 5 to 16 mol ethyleneoxide to coconut or tallow fatty alcohols, to oleyl alcohol, as well as to mono-, di- or trialkylphenols, and also to monoalkylcyclohexanols with 16 to 14 carbon atoms in the alkyl residues. As amphoteric surfactants, the derivatives of secondary or tertiary aliphatic amines come under consideration, wherein the aliphatic groups may be straight chain or branched, and one residue contains 8 to 18 carbon atoms, and another contains a solubilizing anionic group, for example a carboxy, sulfo, sulfato, phosphato or phosphono group.

Builders may also be present in the antimicrobial agents; suitable builders include inorganic or organic salts, especially inorganic or organic complexing agents. Usable compounds include, for example ortho-, pyro- and tripolyphosphates of the alkali metals, the alkali salts of the complex-forming aminocarboxylic acids such as nitrilotriacetic acid and ethylenediaminetetraacetic acid, the alkali salts of complex-forming phosphonic acids such as 1-hydroxyethane-1,1-diphosphonic acids, aminotrimethylenephosphonic acid and ethylenediaminetetramethylenephosphonic acid, as well as the alkali salts of sulfodicarboxylic acids, lactic acid, citric acid and tartaric acid. Other builder substances coming under consideration are the acidic, water-soluble salts of higher molecular weight polycarboxylic acids, for example polymers of maleic acid, itaconic acid, fumaric acid and citric acid. Also, mixed polymers of these acids with one another or with other polymerizable substances, for example ethylene, propylene, acrylic acid, vinyl acetate, isobutylene, acrylamide and styrene are usable. If the antimicrobial agents contain organic solvents, the addition of solubilizing agents such as benzenesulfonic acid, toluenesulfonic acid and xylenesulfonic acid in the form of their alkali salts may be indicated.

The content of substances in accordance with the invention in the ready to use antimicrobial agents is between 0.01 and 5 wt-%, based on the total quantity of agent. To produce such ready-to-use agents, concentrates or solid mixtures may be prepared which contain up to 50 wt-% active ingredient.

In addition, the substances in accordance with the invention can be utilized for the preservation of industrial products which show a tendency toward attack by bacteria and fungi or other microbial destruction, for example, pastes, sizes, dispersion dyes, as well as cutting and drilling oils. For this intended application in general the addition of 0.01 to 2 wt-% based on the material to be preserved is sufficient.

EXAMPLES

A. Preparation of the 2,2-dibromo-3-oxonitriles

EXAMPLE 1

In an agitator vessel with an agitator, dropping funnel, gas inlet tube and attached distillation column, under agitation and introduction of nitrogen, 130.2 g (1 mol) methyl caproate and 548 g (13.4 mol) acetonitrile are heated to the boiling point. In the boiling reaction solution, 180 g of 30 wt-% sodium methylate solution (54 g=1 mol sodium methylate) were dropped over a period of 2 hr. Methanol originating from the sodium methylate solution and formed during the reaction was simultaneously distilled off, together with acetonitrile, over the distillation column. After the end of the addition of sodium methylate solution, the distillation was continued until the boiling point of pure acetonitrile became established in the column head and the splitting off of methanol was complete. During distillation a total of 640 g distillate was obtained, which according to gas chromatographic investigation consisted of 24.1 wt-% methanol and 75.9 wt-% acetonitrile.

The sodium enolate salt of 3-oxooctanenitrile precipitating upon cooling of the reaction mixture was removed by filtration and washed with acetone. In this process, 134 g (83% of the theoretical) of a white salt were obtained.

For conversion into the free 3-oxooctanenitrile, 27.6 g (0.17 mol) of the sodium enolate salt were stirred into a mixture of 100 ml ice water and 58 ml of a 10 wt-% hydrochloric acid, and [the mixture] acidified to pH 4. The 3-oxooctanenitrile that separated out was taken up in methyl-tert-butyl ether; the separated organic phase was washed with water until neutral and dried over sodium sulfate. Following distillation of the methyl-tert-butyl ether, 22.5 g (93% of the theoretical) 3-oxooctanenitrile were left behind, which according to gas chromatographic analysis had a purity of 98 wt-%.

In an agitator vessel, under agitation, ice cooling and introduction of nitrogen, to 13.9 g (0.1 mol) 3-oxooctanenitrile, dissolved in 75 ml methylene chloride, and 22 g (0.22 mol) potassium hydrogen carbonate, dissolved in 75 ml water, at 10° to 15° C. in the course of 90 min, 35.2 g (0.22 mol) bromine, dissolved in 40 ml methylene chloride, were dropped in. The mixture produced was further agitated for 4 hr at room temperature to complete the reaction. Then the methylene chloride phase was separated. Excess bromine was removed with some sodium hydrogen sulfite. Then the solution was washed with water until neutral and dried over sodium sulfate. The crude product remaining after distilling off the methylene chloride was distilled over a thin layer evaporator at 95° C./0.01 mbar. In this process 22.1 g (75% of the theoretical) 2,2-dibromo-3-oxooctanenitrile (Substance A) was obtained as a yellowish oil with $n_D^{20} = 1.5055$, which according to gas chromatographic analysis had a degree of purity of 97.2 wt-%.

Analysis $C_8H_{11}NOBr_2$ (MW 296.989): calculated (%): 32.35 C; 3.73 H; 4.72 N; 53.81 Br. found (%): 31.9 C; 3.2 H; 5.0 N; 53.5 Br.

$^1$H-NMR-spectrum (60 MHz; $CDCl_3$) =3.10 (t); 1.75 (m); 1.35 (m); 0.90 (t).

The substances B through E were produced analogously.

Substance B: 2,2-dibromo-3-oxodecanenitrile

Yellowish oil with $n_D^{20} = 1.4978$; b.p. 120° C./0.01 mbar.

Analysis $C_{10}H_{15}NOBr_2$ (MW 325.042): calculated (%): 36.95 C; 4.65 H; 4.31 Br; 49.17 Br. found (%): 37.5 C; 4.65 H; 4.45 Br; 49.3 Br.

$^1$H-NMR-spectrum (90 MHz; $CDCl_3$) =3.01 (t); 1.72 (m); 1.30 (m); 0.87 (t).

$^{13}$C-NMR-spectrum (50 MH$_2$ [sic]; $CDCl_3$) =189.48 (s); 113.53 (s); 34.02 (t); 33.87 (s); 31.53 (t); 28.80 (t); 28.62 (t); 24.64 (t); 22.53 (t); 14.01 (q).

Substance C: 2,2-dibromo-3-oxododecanenitrile

Yellowish oil with $n_D^{20} = 1.4956$

Analysis $C_{12}H_{19}ONBr_2$ (MW 353.096): calculated (%): 40.82 C; 5.42 H; 3.97 N; 45.26 Br. found (%): 41.2 C; 5.16 H; 3.97 N; 45.4 Br.

Substance D: 2,2-dibromo-3-oxotetradecanenitrile

Colorless crystals; m.p. 34° C.

Analysis $C_{14}H_{23}ONBr_2$ (MW 381.15); calculated (%): 44.12 C; 6.08 H; 3.67 N; 41.93 Br. found (%): 44.2 C; 6.45 H; 3.72 N; 42.6 Br.

Substance E: 2,2-dibromo-3-oxoeicosanenitrile

Colorless crystals with m.p. 57° C.

Analysis $C_{20}H_{35}NOBr_2$ (MW 465.32); calculated (%): 51.62 C; 7.58 H; 3.01 N; 34.35 Br. found (%): 51.8 C.

EXAMPLE 2

Into an agitation apparatus with agitator, dropping funnel, gas inlet tube and reflux cooler, under agitation and introduction of nitrogen, 28.8 g (0.6 mol) sodium hydride (as a 50 wt-% suspension in white oil) suspended in 200 ml absolute toluene and 49.9 g (0.3 mol) 2-methoxybenzoic acid methyl ester were introduced. The mixture was heated to 85° C. Within 2 hr, 24.6 g (0.5 mol) absolute acetonitrile was dropped into the heated mixture. Then the reaction mixture was further agitated for 15 hr at 90° C. The mixture was then cooled to 0° C., 300 ml ice water were added carefully under vigorous agitation, and then agitation was continued for 1 hr at 0° C. Then the aqueous phase was removed and extracted with 100 ml toluene. After cooling to 0° C. the aqueous phase was acidified with dilute hydrochloric acid to pH 1. The precipitated product was washed with ice water and dried. The crude product (44 g) was recrystallized from isopropanol; 37.9 g (72% of the theoretical) 2-methoxybenzoylacetonitrile with m.p. 85°–88° were obtained.

8.7 g (0.05 mol) 2-methoxybenzoylacetonitrile were dissolved in 70 ml methylene chloride. Following addition of a solution of 20 g potassium hydrogen carbonate in 100 ml water, the mixture was cooled to −5° C. before 17.6 g (0.11 mol) bromine in 30 ml methylene chloride were dropped in under vigorous agitation within 2 hr. After the addition of bromine was complete, the reaction mixture was further agitated for 90 min at −5° to 0° C. Then, excess bromine was removed by adding hydroxylamine hydrochloride; the organic phase was separated, washed twice with 100 ml water each, and dried over magnesium sulfate. Following evaporation of the solvent under vacuum, 15.5 g (93% of the theoretical) 2-methoxybenzoyldibromoacetonitrile (Substance J) were left behind as a yellow oil with $n_D^{20} = 1.5948$.

Analysis $C_{10}H_7HO_2Br_2$ (MW 333.006); calculated (%): 36.07 C; 2.12 H; 4.21 N; 47.99 Br. found (%): 35.90 C; 1.97 H; 4.11 N; 47.80 Br.

$^1$N-NMR-spectrum (60 MHz; CDCl$_3$) =3.92 (s); 6.95–7.77 (m).

IR (film): 1730 cm$^{-1}$.

The substances F through I and K through O were prepared analogously.

Substance F: Benzoyldibromoacetonitrile
Yellowish oil with $n_D^{20} = 1.5982$; b.p. 120° C./0.01 mbar (thin layer evaporator).

Analysis $C_9H_5NOBr_2$ (MW 302.952); calculated (%): 35.68 C; 1.66 H; 4.62 N; 52.75 Br. found (%): 34.0 C; 1.5 H; 4.7 N; 53.8 Br.

$^1$H-NMR-spectrum (60 MHz; CDCl$_3$) =8.19 (d,d); 7.59–7.33 (m).

$^{13}$C-NMR-spectrum (50 MHz; CDCl$_3$) =179.9 (s); 135.2 (d); 131.2 (d); 128.8 (d) 128.4 (s); 114.1 (s); 31.4 (s).

Substance G: 2-methylbenzoyldibromoacetonitrile
Yellowish oil with $n_D^{20} = 1.5949$ Analysis $C_{10}H_7NOBr_2$ (MW 317.006); calculated (%): 37.89 C; 2.23 H; 4.42 N; 50.42 Br. found (%): 39.90 C; 1.65 H; 4.46 N; 50.60 Br.

Substance H: 3-methylbenzoyldibromoacetonitrile
Yellowish oil with $n_D^{20} = 1.5991$ Analysis $C_{10}H_7NOBr_2$ (MW 317.006) calculated (%): 37.89 C; 2.23 H; 4.42 N; 50.42 Br. found (%): 38.20 C; 1.99 H; 4.38 N; 51.5 Br.

Substance I: 4-methylbenzoyldibromoacetonitrile
Colorless crystals; m.p. 65°–69° C.

Analysis $C_{10}H_7NOBr_2$ (MW 317.006); calculated (%): 37.89 C; 2.23 H; 4.42 N; 50.42 Br. found (%): 37.40 C; 2.11 H; 4.39 N; 50.40 Br.

Substance K: 3-methoxybenzoyldibromoacetonitrile
Yellowish oil with $n_D^{20} = 1.6048$ Analysis $C_{10}H_7NOBr_2$ (MW 317.006); calculated (%): 36.07 C; 2.12 H; 4.21 N; 47.99 Br. found (%): 36.00 C; 2.07 H; 4.26 N; 48.8 Br.

Substance L: 4-methoxybenzoylbromoacetonitrile
Colorless crystals; m.p. 57°–62° C.

Analysis $C_{10}H_7NO_2Br_2$ (MW 333.006); calculated (%): 36.07 C; 2.12 H; 4.21 N; 47.99 Br. found (%): 35.80 C; 2.09 H; 4.26 N; 47.60 Br.

Substance M: 4-bromobenzoyldibromoacetonitrile
Colorless crystals; m.p. 38°–44° C.

Analysis $C_9H_4NOBr_3$ (MW 381.887); calculated (%): 28.31 C; 1.06 H; 3.67 N; 62.78 Br. found (%): 27.90 C; 0.96 H; 3.66 N; 61.90 Br.

Substance N: 1-naphthoyldibromoacetonitrile
Colorless crystals; m.p. 48°–51° C.

Analysis $C_{13}H_7NOBr_2$ (MW 353.036) calculated (%): 44.23 C; 2.00 H; 3.97 N; 45.27 Br. found (%): 43.20 C; 1.91 H; 3.80 N; 44.8 Br.

Substance O: 2-naphthoyldibromoacetonitrile
Colorless crystals; m.p. 61°–67° C.

Analysis $C_{13}H_7NOBr_2$ (MW 353.036) calculated (%): 44.23 C; 2.00 H; 3.97 N; 45.27 Br. found (%): 43.50 C; 1.91 H; 3.75 N; 45.00 Br.

The 2,2-dibromo-3-oxonitriles prepared according to Examples 1 and 2 are summarized in Table I below along with their physical data.

TABLE I 2,2-Dibromo-3-oxonitriles of formula R—CO—CBr$_2$—CN

| Substance | R | b.p. (°C./mbar) | m.p. (°C.) | $n_D^{20}$ |
|---|---|---|---|---|
| A | n-C$_5$H$_{11}$ | 95/0.01 | oil | 1.5055 |
| B | n-C$_7$H$_{15}$ | 120/0.01 | oil | 1.4978 |
| C | n-C$_9$H$_{19}$ | — | oil | 1.4956 |
| D | n-C$_{11}$H$_{23}$ | — | 34 | — |
| E | n-C$_{17}$H$_{35}$ | — | 57 | — |
| F | phenyl | 120/0.01 | — | 1.5982 |
| G | 2-methylphenyl | — | oil | 1.5949 |
| H | 3-methylphenyl | — | oil | 1.5991 |
| I | 4-methylphenyl | — | 65–69 | — |
| J | 2-methoxyphenyl | — | oil | 1.5948 |
| K | 3-methoxyphenyl | — | oil | 1.6048 |
| [L] | 4-methoxyphenyl | * | * | * |
| M | 4-bromophenyl | — | 38–44 | — |
| N | 1-naphthyl | — | 48–51 | — |
| O | 2-naphthyl | — | 61–67 | — |

B. Antimicrobial Activity
1. Microbistatic Activity

The microbistatic activity of the substances A to O in accordance with the invention was determined with respect to the following test organism suspensions:
1. *Staphylococcus aureus*: $2 \times 10^9$ organisms/ml
2. *Escherichia coli*: $2 \times 10^9$ organisms/ml
3. *Pseudomonas aeruginosa*: $5 \times 10^8$ organisms/ml
4. *Candida albicans*: $2 \times 10^8$ organisms/ml
5. *Aspergillus niger*: $5 \times 10^7$ organisms/ml
6. *Penicillium camerunense*: $5 \times 10^7$ organisms/ml.

The inhibiting concentrations of the compounds to be investigated were determined with the aid of the dilution test according to the Guidelines for the Testing of Chemical Disinfectants of the German Association for Hygiene and Microbiology (1972). The experiments were performed in sterile test tubes, which for organisms 1 through 3 contain standard I broth (pH 7.5, Merck) and for organisms 4 through 6, malt broth (pH 5.5, Merck). Following addition of the active ingredients, the nutrient solution volume in the tubes was 5 ml in each case. Then in each case 0.1 ml of the test organism suspension of the indicated concentration was placed in the tubes. The nutrient solution samples inoculated with bacteria were stored in an incubator at 37° C. for 3 days. The samples inoculated with fungi were incubated for 4 days at 30° C. Then the concentration of active ingredient added to the nutrient medium which just inhibited the growth of the organisms was ascertained. The value obtained in this way was designated as the inhibiting concentration. The following active ingredient concentrations in ppm were tested: 1000, 500, 250, 100, 50 and 10.

The inhibiting concentrations presented in Table II below were determined for the substances A to O.

TABLE II

INHIBITING CONCENTRATIONS (IN PPM) OF THE SUBSTANCES A THROUGH O IN THE DILUTION TEST.

| Substance | Test organism | | | | | |
|---|---|---|---|---|---|---|
| | 1 | 2 | 3 | 4 | 5 | 6 |
| A | 50 | 100 | 100 | 50 | 50 | 50 |
| B | 50 | 100 | 100 | 50 | 50 | ≦10 |
| C | 50 | 100 | 100 | 50 | 50 | 50 |
| D | 50 | 100 | 100 | 50 | 50 | 50 |
| E | | | | | | |
| F | 100 | 50 | 50 | 50 | ≦10 | ≦10 |
| G | 100 | 250 | 500 | 100 | 50 | 50 |
| H | 100 | 100 | 100 | 50 | ≦10 | ≦10 |
| I | 100 | 100 | 100 | 50 | 50 | 50 |
| J | 100 | 250 | 100 | 50 | 50 | 50 |
| K | 100 | 100 | 100 | 50 | 50 | 50 |
| L | 100 | 100 | 100 | 50 | 50 | 50 |
| M | 100 | 100 | 100 | 50 | 50 | 50 |
| N | 250 | 500 | 500 | 100 | 50 | 50 |
| O | 100 | 100 | 100 | 100 | ≦10 | ≦10 |

2. Microbicidal Activity

The microbicidal activity of the substances A through O in accordance with the invention was determined with respect to the following test organism suspensions:
1. *Staphylococcus aureus*: $2 \times 10^9$ organisms/ml
2. *Escherichia coli*: $2 \times 10^9$ organisms/ml
3. *Pseudomonas aeruginosa*: $5 \times 10^8$ organisms/ml
4. *Candida albicans*: $2 \times 10^8$ organisms/ml
5. *Aspergillus niger*: $5 \times 10^7$ organisms/ml
6. *Penicillium camerunense*: $5 \times 10^7$ organisms/ml.

TABLE III

KILLING TIMES OF SUBSTANCES A TO O IN THE SUSPENSION TEST.

| Substance | Conc. (ppm) | Test organism | | | | | |
|---|---|---|---|---|---|---|---|
| | | 1 | 2 | 3 | 4 | 5 | 6 |
| A | 2000 | ≦15 | ≦15 | ≦15 | ≦15 | ≦15 | ≦15 |
| | 500 | ≦15 | 60 | 60 | ≦15 | ≦15 | 60 |
| B | 2000 | ≦15 | ≦15 | ≦15 | ≦15 | ≦15 | ≦15 |
| | 500 | ≦15 | 60 | 60 | 60 | ≦15 | 60 |
| C | 2000 | ≦15 | ≦15 | ≦15 | ≦15 | ≦15 | ≦15 |
| | 500 | ≦15 | 60 | ≦15 | ≦15 | ≦15 | 60 |
| D | 2000 | ≦15 | +++ | 60 | 60 | 60 | +++ |
| | 500 | 60 | +++ | +++ | +++ | +++ | +++ |
| E | | | | | | | |
| F | 2000 | ≦15 | ≦15 | ≦15 | ≦15 | ≦15 | ≦15 |
| | 500 | + | 60 | ≦15 | 60 | 60 | 60 |
| G | 2000 | 60 | +++ | 60 | 60 | ++ | +++ |
| | 500 | + | +++ | +++ | +++ | +++ | +++ |
| H | 2000 | 60 | 60 | ≦15 | ≦15 | 60 | ≦15 |
| | 500 | ++ | ++ | 60 | ++ | +++ | +++ |
| I | 2000 | 60 | 60 | ≦15 | 60 | 60 | ++ |
| | 500 | + | ++ | 60 | ++ | ++ | +++ |
| J | 2000 | 60 | 60 | ≦15 | ≦15 | 60 | ≦15 |
| | 500 | +++ | +++ | + | +++ | +++ | +++ |
| K | 2000 | ++ | 60 | ≦15 | 60 | + | ≦15 |
| | 500 | +++ | +++ | +++ | +++ | +++ | +++ |
| L | 2000 | +++ | 60 | ≦15 | 60 | 60 | +++ |
| | 500 | +++ | + | 60 | ++ | ++ | +++ |
| M | 2000 | 60 | 60 | ≦15 | ≦15 | 60 | +++ |
| | 500 | +++ | ++ | 60 | 60 | +++ | +++ |
| N | 2000 | ≦15 | 60 | 60 | 60 | ++ | +++ |
| | 500 | 60 | 60 | 60 | 60 | ++ | +++ |
| O | 2000 | ≦15 | ≦15 | ≦15 | ≦15 | ≦15 | ++ |
| | 500 | ≦15 | ≦15 | ≦15 | ≦15 | 60 | +++ |

The killing time of the product to be investigated were determined with the aid of the suspension test. Using water with a hardness of 17° dH, test solutions were prepared containing 2000 or 500 ppm active ingredient. At room temperature in each case 0.1 ml test organism suspension was pipetted into test tubes and mixed with 10 ml of the above described test solutions in each case. After various contact times up to 60 min, ca. 0.05 ml of material were taken from the test tubes using an inoculating loop and spread on a nutrient agar which contained 3% Tween 80 and 0.3% lecithin as inhibition removers. For organisms 1 to 3 the nutrient medium consisted of 2.5 wt-% standard I broth (Merck), and for organisms 4 to 6, of malt broth pH 5 (Merck), each of which contained 1.2 wt-% agar for solidification. The samples were incubated at 37° C. and 30° C. respectively. After 2-3 days the cultures were evaluated macroscopically for growth, and in this way the killing time or the residual organism content was determined. The results thus obtained are reproduced in Table III.

In Table III, "+" means less than 50, "++" means less than 200, and "+++" means more than 200 surviving organisms after 60 min contact time. The numerical values given in the individual columns represent the contact time in min.

We claim:

1. 2,2-Dibromo-3-oxonitriles of formula I $$R-CO-CBr_2-CN \qquad (I)$$

wherein R represents a straight chain or branched alkyl group with 5 to 21 carbon atoms, a cycloaliphatic group unsubstituted or substituted with at least one alkyl group, and having 3 to 6 ring carbon atoms, or a phenyl or naphthyl group unsubstituted or substituted with at least one alkyl group, alkoxy group, fluorine or bromine atom, or nitro group.

2. The 2,2-dibromo-3-oxonitrile of claim 1 where R is a cycloaliphatic group unsubstituted or substituted with at least one alkyl group and having 3 to 6 ring carbon atoms.

3. The 2,2-dibromo-3-oxonitrile of claim 1 wherein R is a straight chain or branched alkyl group with 5 to 21 carbon atoms.

* * * * *